United States Patent [19]

Buckler et al.

[11] Patent Number: 4,472,301

[45] Date of Patent: Sep. 18, 1984

[54] PROPRANOLOL IMMUNOGEN AND ANTIBODIES

[75] Inventors: Robert T. Buckler, Edwardsburg, Mich.; Robert J. Carrico, Elkhart, Ind.

[73] Assignee: Miles Laboratories, Inc., Elkhart, Ind.

[21] Appl. No.: 383,340

[22] Filed: May 27, 1982

[51] Int. Cl.³ .................. C07G 7/00; A61K 39/00
[52] U.S. Cl. ..................... 260/112 B; 260/112 R; 260/121; 424/85; 435/7
[58] Field of Search ............... 260/112 R, 112 B, 121

[56] References Cited

U.S. PATENT DOCUMENTS

| | | |
|---|---|---|
| 3,654,090 | 4/1972 | Schuurs et al. ............... 195/103.5 |
| 3,817,837 | 6/1974 | Rubenstein et al. ......... 195/103.5 R |
| 3,935,074 | 1/1976 | Rubenstein et al. ......... 195/103.5 R |
| 3,996,345 | 12/1976 | Ullman et al. .................... 424/12 |
| 3,998,943 | 12/1976 | Ullman .............................. 424/12 |
| 4,026,879 | 5/1977 | Spector ............................ 260/121 |
| 4,070,492 | 1/1978 | Spector ............................. 424/1 |
| 4,133,639 | 1/1979 | Harte ............................. 23/230 B |
| 4,134,792 | 1/1979 | Boguslaski et al. ................ 195/99 |
| 4,160,016 | 7/1979 | Ullman ............................... 424/8 |
| 4,171,311 | 10/1979 | Araps ........................... 260/326.34 |
| 4,201,763 | 5/1980 | Monthony et al. .................. 424/8 |
| 4,238,195 | 12/1980 | Boguslaski et al. ............. 23/230 B |
| 4,238,565 | 12/1980 | Hornby et al. ...................... 435/7 |
| 4,241,177 | 12/1980 | Singh et al. ........................ 435/7 |
| 4,273,866 | 6/1981 | Voss et al. ......................... 435/7 |
| 4,279,992 | 7/1981 | Boguslaski et al. ................ 435/7 |
| 4,332,787 | 6/1982 | Homcy et al. ............. 260/112 B X |

FOREIGN PATENT DOCUMENTS 1552609 9/1979 United Kingdom .

OTHER PUBLICATIONS

*Drug Metab. Rev.*, 10:271 (1979), Weinryb & Shroff, "Metabolic & Analytic Considerations . . . Immunoassays".
*Br. Med. Bull.*, 30:24–31 (1974), J. H. L. Playfiar et al., "Production of Antibodies & Binding Reagents".
*Clin. Chem.*, 22(6):726 (1976), A. Broughton & J. E. Strong, "Radioimmunoassay of Antibiotics & Chemotherapeutic Agents".
*J. of Immun. Methods*, 7:1 (1975), P. Butler, Jr., "Drug Immunoassays".
*J. Biol. Chem.*, 244(2):406 (1969), P. Cuathrecasas et al., "Cross-Linking of Aminotyrosyl Residues . . . Nuclease".
*Endocrin.*, 87:1055 (1970), L. A. Frohman et al., "Immunologic & Biologic Properties of . . . Polymer".
*Biochem. Biophys. Res. Comm.*, 23:730 (1966), A. Dutton et al., "Bifunctional Imidoesters As Cross-Linking Reagents".
*Nature*, 216:514 (1967), G. Kay et al., "Coupling of Enzymes to Cellulose using Chloro-s-triazines".
*Biochem. J.*, 173:723 (1978), J. Carlsson et al., "Protein Thiolation & Reversible . . . Conjugation".
*Biochem.*, 20:4229 (1981), F. J. Martin et al., "Immunospecific Targeting of Liposomes to Cells: . . . Bonds".
*J. Amer. Chem. Soc.*, 93:2897 (1971), R. F. Borch et al., "The Cyanohydridoborate Anion as a Selective Reducing Agent".
*Europ. J. Med. Chem.*, 12:465 (1977), R. T. Buckler et al., "The Synthesis and Biological Activity . . . $F_{2\alpha}$".
*Nature*, 266:495 (1977), K. L. Welsh, "Antibody Production Made Easier".
*Science*, 208:692 (1980), N. Wade, "Hybridomas: A Potent New Biotechnology".
*Methods in Enzymol.*, 73:3 (1981), G. Galfre et al., "Preparation of Monoclonal Antibodies: . . . ".
*J. Exp. Med.*, 122:1029 (1965), W. B. Dandliker et al., "Study of Penicillin Antibodies . . . Immunodiffusion".
*J. Chem. Soc.*, pp. 1571–1577 (1954), O. Stephenson, "The Condensation of Epichlorohydrin . . . with Catechol".
*Clinica Chimica Acta*, 57:263 (1974), C. Bohuon et al., "Radioimmunoassay of Methotrexate in Biological Fluids".
*Anal. Biochem.*, 1:66 (1960), J. D. Mandell et al., "A Fractionating Column for . . . Acids".
*Clin. Chem.*, 23(8):1402 (1977), J. F. Burd et al., "Homogeneous Reactant-Labeled . . . Human Serum".

Primary Examiner—John Kight
Assistant Examiner—Garnette D. Draper
Attorney, Agent, or Firm—Andrew L. Klawitter

[57] ABSTRACT

A propranolol immunogen comprising an unsubstituted hydroxypropylamine precursor of propranolol coupled through a bis-imidate linking group to an immunogenic carrier material. The immunogen is useful to stimulate the production of antibodies which recognize propranolol and can perform as reagents in immunoassays to determine propranolol.

8 Claims, No Drawings

PROPRANOLOL IMMUNOGEN AND ANTIBODIES

BACKGROUND OF THE INVENTION

1. Field of the Invention:

To produce its desired characteristic effects, a pharmacologically active drug must be present in appropriate concentrations at its sites of action. The concentration of a drug in vivo is not only a function of the amount of drug administered, but is also a function of the extent and rate of its adsorption, distribution, binding in tissues, biotransformation and excretion. In order to determine the proper dosage for therapeutic efficacy, it is necessary to determine the level of drug in a physiologic fluid, e.g., blood or urine.

The determination of drugs can be accomplished by various techniques, including fluorometry, gas-liquid chromatography, mass spectroscopy and competitive protein binding assays ("immunoassays"). Immunoassay techniques for drug level determination in physiologic fluids have become increasingly used for a wide variety of drugs, because such techniques are extremely sensitive, specific, and technically adaptable to processing clinical samples. Immunoassay techniques involve the use of antibodies which are specific to the drug, i.e., which bind with high affinity to the drug, but do not bind, or bind weakly, to related drugs and metabolites which may be present in the physiologic fluid.

A hapten is defined as a small molecule which by itself cannot stimulate antibody production, but can stimulate antibody production when coupled to an immunogenic carrier. The state-of-the-art of preparing antibodies to haptens such as drugs is represented by Weinryb et. al., *Drug Metabolism Reviews*, 10(2):271 (1979); Playfair et. al., *Br. Med. Bull.* 30:24 (1974); Broughton et. al., *Clin. Chem.*, 22/6:726 (1976); and Butler, *J. Immunol. Meth.*, 7:1 (1975).

One type of drug which can be assayed by such techniques is propranolol.

Propranolol is a β-adrenergic inhibitor having the formula:

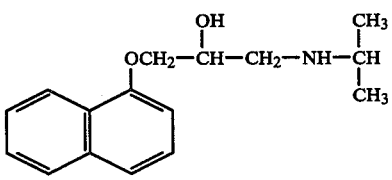

Propranolol is widely used in therapy of numerous disorders, including hypertension, rhythm disturbances of the heart, angina pectoris, and hyperthyroidism. It has been found that individual variability in the level of propranolol present in the plasma, even at the same dosage levels, is common. There is also great variability in the extent to which the drug is metabolized in the liver. Consequently, it is not always possible to predict the plasma concentration or the effect of propranolol after a particular dose is administered. Because of these factors, the immunoassay technique has been found to be a clinically useful method of determining cirulatory levels of propranolol.

2. Description of the Prior Art

U.S. Pat. No. 4,026,879 is directed to an immunogen of propranolol which is propranolol coupled at the hydroxyl group through a bridging arm to an immunogenic carrier material. The immunogen claimed has the structure:

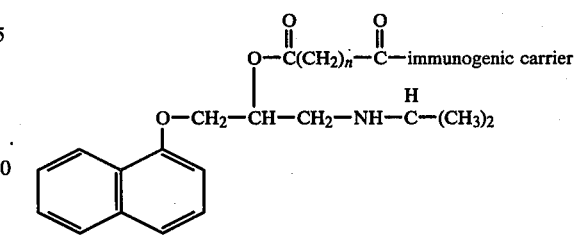

U.S. Pat. No. 4,070,492 is directed to a propranolol antibody prepared by injecting a host animal with the immunogen claimed in U.S. Pat. No. 4,026,879.

U.S. Pat. No. 4,241,177 is directed to an immunogen of propranolol which is the propranolol coupled at the amine nitrogen through a binding arm (R) to an immunogenic carrier material. The claimed immunogens have the structure:

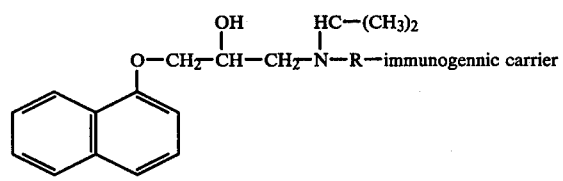

SUMMARY OF THE INVENTION

The present invention provides reagents for use in propranolol immunoassays. The invention includes 3-(1-naphthoxy)-2-hydroxypropylamine immunogen having the formula:

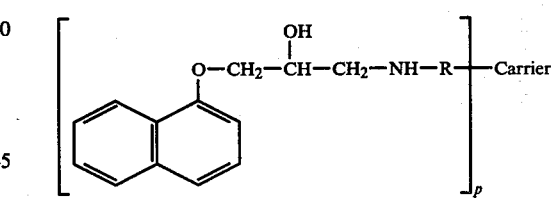

wherein R is a linking group, Carrier is an immunogenic carrier material, and p is on the average from about 1 to 50; and 3-N-[2-hydroxy-3-(1-naphthoxy)-1-propyl] aminobutyric acid immunogen having the formula:

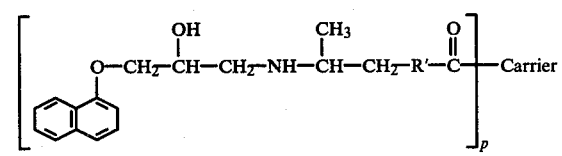

wherein R' is an alkylene, alkenylene or phenylene moiety, having from 1 to 12 carbon atoms.

The invention also includes antibodies prepared against the above immunogens; a labelled conjugate of 3-N-[2-hydroxy-3-(1-naphthoxy)-1-propyl] aminobutyric acid; intermediates used in the synthesis of the above immunogens; an immunoassay method; a test kit and test device.

DETAILED DESCRIPTION OF THE INVENTION

The present invention relates to an immunoassay for propranolol, using antibodies against propranolol which are prepared by injecting an animal with an immunogen which is a propranolol derivative coupled to an immunogenic carrier. The propranolol derivative is 3-(1-naphthoxy)-2-hydroxypropylamine, or 3-N-[2-hydroxy-3-(1-naphthoxy)-1-propyl] aminobutyric acid coupled to an immunogenic carrier.

The hydroxypropylamine-immunogen has the formula:

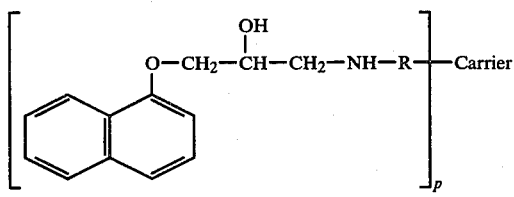

wherein R, p and Carrier are as defined earlier.

The aminobutyric acid-immunogen has the formula:

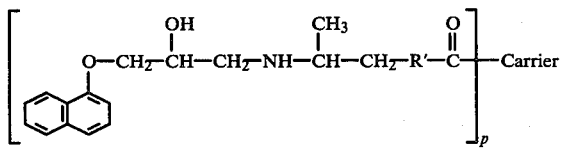

wherein R', p and Carrier are as defined earlier.

Alternately, the intermediate can be used to form labelled conjugates which serve as the detectable reagents in propranolol immunoassays.

The immunogenic carrier material can be selected from any of those conventionally known. In most cases, the carrier will be a protein or polypeptide, although other materials such as carbohydrates, polysaccharides, lipopolysaccharides, nucleic acids and the like of sufficient size and immunogenicity can likewise be used. For the most part, immunogenic proteins and polypeptides will have molecular weights between 5,000 and 10,000,000, preferably greater than 15,000, and more usually greater than 50,000. Generally, proteins taken from one animal species will be immunogenic when introduced into the blood stream of another species. Particularly useful proteins are albumins, globulins, enzymes, hemocyanins, glutelins, proteins having significant nonproteinaceous constituents, e.g., glycoproteins, and the like. The albumins and globulins of molecular weight between 30,000 and 200,000 are particularly preferred. Further reference to the state-of-the-art concerning conventional immunogenic carrier materials and techniques for coupling haptens thereto may be had to the following: Parker, *Radioimmunoassay of Biologically Active Compounds*, Prentice-Hall (Englewood Cliffs, N.J. U.S.A., 1976); Butler, *J. Immunol. Meth.*, 7:1 (1975); Weinryb and Shroff, *Drug Metab. Rev.*, 10(2):271 (1979): Broughton and Strong, *Clin. Chem.*, 22(6):726 (1976); and Playfair, et al., *Br. Med. Bull.*, 30:24 (1974).

The designation p refers to the average number of propranolol residues conjugated to the carrier. The number p is sometimes referred to as the epitopic density of the immunogen and in the usual situation will be on the average from 1 to about 50, more normally from 1 to about 25. Optimal epitopic densities, considering the ease and reproducibility of synthesis of the immunogen and antibody response, fall between about 2 and about 20, more usually 5 and 15.

The hydroxypropylamine can be coupled to the immunogenic carrier through a linking group R by techniques well known in the art. For example, the amino group of the drug moiety can be attached to amino-containing immunogenic carriers, such as proteins, by difunctional reagents such as toluene-2,4-diisocyanate [C. H. W. Hirs and S. N. Timasheff, *Methods in Enzymol.*, 25 (Part B):625 (1972)]; 4,4'-difluoro-3,3'-dinitro diphenyl sulfone [P. Cuatrecasas, et. al., *J. Biol. Chem.*, 244:406 (1969)]; glutaraldehyde [L. A. Frohman, et. al., *Endocrinol.*, 87:1055 (1970)]; bis-imidoesters [A. Dutton, et. al., *Biochem. Biophys. Res. Comm.*, 23:730 (1966)]; or chlorotriazine [G. Kay and E. M. Crook, *Nature*, 216:514 (1967)].

Alternatively the amino group of the hydroxy propylamine can be coupled to carboxyl functions present in the carrier by standard peptide bond forming reactions such as are described in "Peptides" ed. Goodman and Meienhofer, John Wiley & Sons, (New York, 1977) p. 6 et seq. Additionally, a thiol group may be introduced into the drug derivative by reacting the amino group with N-succimidyl 3-(2-pyridyldithio) propionate [J. Carlsson, et. al., *Biochem. J.*, 173:723 (1978)] and this coupled to thiol containing carrier by the disulfide exchange reaction [Martin, et al., *Biochem.*, 20:4229 (1981)].

This aminobutyric acid can be coupled directly to the immunogen carrier by techniques well-known in the art. For example, the aminobutyric acid can be coupled to immunogen carriers through standard peptide bond forming reactions (Goodman and Meinhofer, supra).

Alternatively, the attachment to the carrier can involve the use of a "spacer" R', as described below, where R' can be from about 1 to 12 carbon atoms.

When R' is alkylene, a reductive alkylation reaction can be employed. The compound

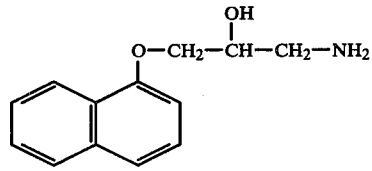

can be reacted with an appropriate keto-alkanoic acid. For example, the above amine and 7-keto octanoic acid [O. Wallach, Ann., 345:141 (1906)] in the presence of sodium cyanoborohydride [R. F. Borch, et al., *J. Amer. Chem. Soc.*, 93:2897 (1971)] will react to give

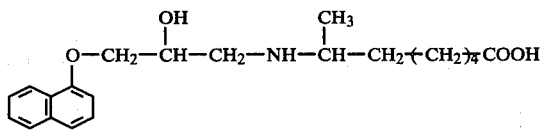

which can be attached to amine-containing carriers by conventional peptide bond-forming reactions.

When R' is alkenylene, the preceding synthesis can be modified to yield an alkenylene linking group by substituting a keto-alkenoic acid for the keto-alkanoic acid.

For example the use of 9-oxo-2-decenoic acid [M. Barbier, et. al., *Compt. Rendu.* 251:1135 (1960)] in the above reductive alkylation reaction will yield

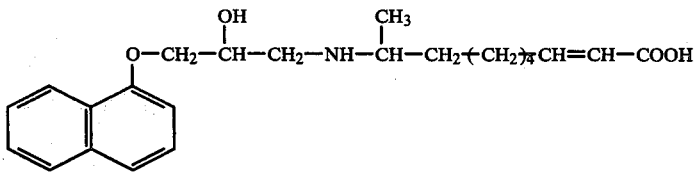

which can be attached to amine containing polymers.

When R' is phenylene, the preceding examples can be modified by replacing the keto-alkanoic or keto-alkenoic acids with the appropriate aromatic keto acid. For example, the amino compound can be reductively alkylated with 4-[2-(3-carboxypropyl)phenyl]-2-butanone [R. T. Buckler, et. al., *European J. Med. Chem.*, 12:465 (1977)] to give a carboxyl-functionalized propranolol derivative containing a phenylene group in the linking arm

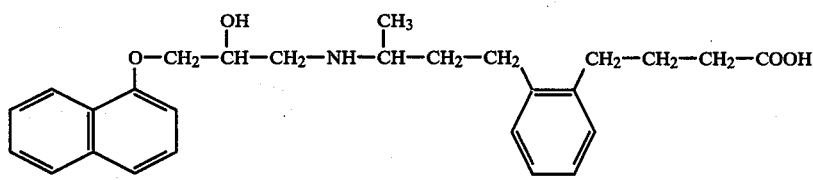

PROPRANOLOL ANTIBODIES

Preparation of specific antibodies using the present immunogen conjugates may follow any conventional technique. Numerous texts are available describing the fundamental aspects of inducing antibody formation, for example reference may be made to Parker, *Radioimmunoassay of Biologically Active Compounds*, Prentice-hall (Englewood Cliffs, N.J. U.S.A., 1976). In the usual case, a host animal such as a rabbit, goat, mouse, guinea pig, or horse is injected at one or more of a variety of sites with the immunogen conjugate, normally in mixture with an adjuvant. Further injections are made at the same site or different sites at regular or irregular intervals thereafter with bleedings being taken to assess antibody titer until it is determined that optimal titer has been reached. The host animal is bled to yield a suitable volume of specific antiserum. Where desirable, purification steps may be taken to remove undesired material such as nonspecific antibodies before the antiserum is considered suitable for use in performing actual assays.

The antibodies can also be obtained by somatic cell hybridization techniques, such antibodies being commonly referred to as monoclonal antibodies. Reviews of such monoclonal antibody techniques are found in *Lymphocyte Hybridomas*, ed. Melchers et. al., Springer-Verlag (New York, 1978), *Nature*, 266:495 (1977), *Science*, 208:692 (1980), and *Methods in Enzymology*, 73(B):3 (1981).

IMMUNOASSAY TECHNIQUES

The antibodies prepared from the 3-(1-naphthoxy)-2-hydroxypropylamine and 3-N-[2-hydroxy-3-(1-naphthoxy)-1-propyl] aminobutyric acid of the present invention can be used in any immunoassay method, and the corresponding reagent means, for determining propranolol, including agglutination techniques, radioimmunoassays, heterogeneous enzyme immunoassays (cf. U.S. Pat. No. 3,654,090), heterogeneous fluorescent immunoassays (cf. U.S. Pat. Nos. 4,201,763; 4,171,311; 4,133,639 and 3,992,631), and homogeneous (separationless) immunoassays. The lattermost are particularly preferred and include such techniques as fluorescence quenching or enhancement (cf. U.S. Pat. No. 4,160,016), fluorescence polarization [(cf. *J. Exp. Med.*, 122:1029 (1965)], enzyme substrate-labelled immunoassay (cf. U.S. Pat. No. 4,279,992 and U.K. Patent Spec. No. 1,552,609), prosthetic group-labelled immunoassay (cf. U.S. Pat. No. 4,238,565), enzyme modulator-labelled immunoassay, e.g., using inhibitor labels (cf. U.S. Pat. Nos. 4,134,792 and 4,273,866), enzyme-labelled immunoassay (cf. U.S. Pat. No. 3,817,837), energy transfer immunoassay (cf. U.S. Pat. No. 3,996,345), chemically-excited fluorescence immunoassay (cf. U.S. Pat. No. 4,238,195) and double antibody steric hindrance immunoassay (cf. U.S. Pat. Nos. 3,935,074 and 3,998,943).

Moreover, the hydroxypropylamine and aminobutyric acid of the present invention can be used to prepare the labelled conjugates needed to perform the various immunoassays described above. Appropriate derivatives can be radiolabelled or labelled with fluorescent moieties in accordance with standard methods. Likewise the appropriate labelling moiety for the preferred homogeneous techniques, e.g., an enzyme substrate, a prosthetic group, an enzyme modulator, or an enzyme (which is a protein and can be coupled similarly to the immunogenic carrier as described above) can be coupled to the hydroxypropylamine to yield labelled conjugates.

A preferred labelled conjugate involving the aminobutyric acid compound is the following β-galactosyl-umbelliferone (βGU)-hydroxypropylamine butyric acid having a piperazine moiety as a linking group:

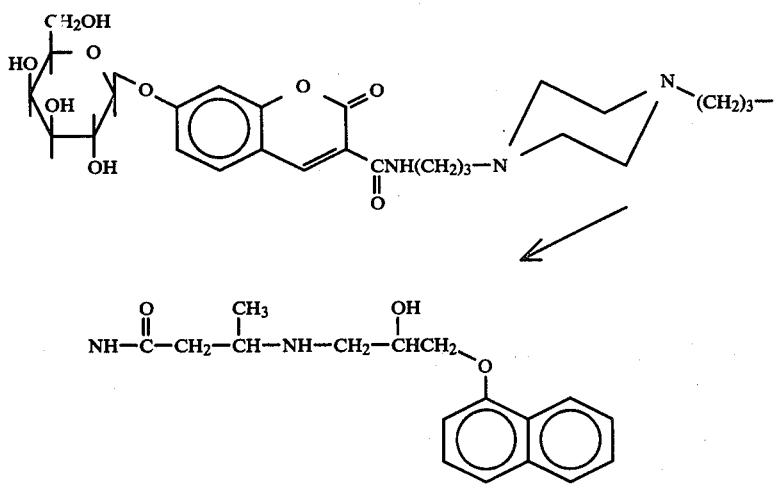

A preferred labelled conjugate involving the hydroxypropylamine compound is the following βGU compound:

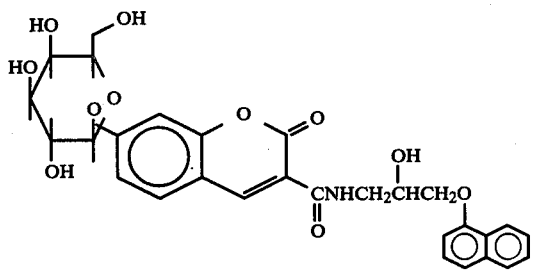

The reagent means of the present invention comprises all of the essential chemical elements required to conduct a desired propranolol immunoassay method encompassed by the present invention. The reagent means is presented in a commercially packaged form, as a composition or admixture where the compatibility of the reagents will allow, in a test device configuration, or as a test kit, i.e., a packaged combination of one or more containers holding the necessary reagents. Included in the reagent means are the reagents appropriate for the binding reaction system desired, e.g., an antibody and labelled conjugate of the present invention. Of course, the reagent means can include other materials as are known in the art and which may be desirable from a commercial and user standpoint, such as buffers, diluents, standards, and so forth. Particularly preferred is a test kit for the homogeneous competitive binding immunoassay of the present invention comprising (a) a propranolol antibody of the present invention, and (b) a labelled hydroxypropylamine conjugate which has a detectable property which is altered when bound with the antibody. Also preferred is a test device comprising a reagent composition including a propranolol antibody of the present invention and a labelled propranolol conjugate which has a detectable property which is altered when bound with the antibody, and a solid carrier member incorporated with the reagent composition. The various forms of such test device are described in U.S. patent application Ser. No. 202,378, filed Oct. 30, 1980, which is incorporated herein by reference. The specific label used in the preferred test kit and test device will depend on the technique followed, as described hereinabove.

The present invention will now be illustrated, but is not intended to be limited, by the following examples.

EXAMPLE I

A. Preparation of 3-(1-Naphthoxy)-2-hydroxy propylamine (NHPA)

Twenty grams (0.14 mol) of 1-naphthol, 38.6 g (0.42 mol) of epichlorohydrin, and 0.4 ml of piperidine were refluxed for 5 hours, then cooled to room temperature (See *J. Chem. Soc.*, 1571, 1954). The reaction mixture was evaporated under reduced pressure to give an oil which was taken up in 50 ml of $CHCl_3$ and stirred for 90 minutes with 50 ml of concentrated HCl. The organic phase was separated, washed with water, washed with saturated NaCl solution, dried, filtered and evaporated. The residue was evaporatively distilled to give 25 g (72 percent yield) of the corresponding chlorohydrin as a viscous yellow oil. This oil was dissolved in 150 ml of dry dimethylformamide (DMF), combined with 28 g (0.15 mol) of potassium phthalimide, and the reaction stirred at reflux for one day. The solvent was removed under reduced pressure and the semi-solid residue triturated with water. Insoluble material present was twice recrystallized from ethanol to give 19 g (55 percent yield) of 1-(1-naphthoxy)-2-hydroxy-3-(N-phthalimide) propane as white needles, mp 154° C.

A solution of 15 g (43 mmol) of the phthalimido propane obtained above and 20 ml of 80 percent hydrazine in 150 ml of methanol was refluxed for 4 hours. The methanol solvent was removed under reduced pressure and the residue stirred for 10 minutes in 300 ml of 0.5 N NaOH. The insoluble material present was then filtered and washed with water. The insoluble material was resuspended in 300 ml of water and stirred for 30 minutes. Filtration and air-drying gave a solid which as recrystallized from toluene to give 6 g (64 percent yield) of 3-(1-naphthoxy)-2-hydroxypropylamine as white plates, mp 106° C.

Analysis: Calculated for $C_{13}H_{15}NO_2$: C, 71.86; H, 6.96; N, 6.45. Found: C. 71.98; H, 6.86, N, 6.24.

B. Preparation of 3-(1-naphthoxy)-2-hydroxypropylamine Bovine Serum Albumin Immunogen and Antibodies Thereto The NHPA prepared as described in A above was coupled to bovine serum albumin by the following procedure. A 83 mg portion of the hydroxypropylamine was mixed with the following and allowed to stand at room temperature from about 1½ to 2 hours: 3 ml methanol, 0.2 ml triethylamine and 188 mg dimethyladipimidate dihydrochloride.

The methanol solvent was then removed in vacuo and the residue was dissolved in 1 ml of fresh methanol. Sixty μl of this solution was added dropwise to a stirred solution containing 100 mg of bovine serum albumin (Miles Laboratories, Elkhart, Ind.) in 3 ml of 0.2 M sodium pyrophosphate buffer, pH 8.5. The mixture was kept at room temperature overnight and chromatographed in a 2.5×55 cm column of Sephadex G25 (Pharmacia Fine Chemicals) equilibrated with 0.1 M sodium phosphate, pH 7.0. The first peak of eluted material with absorbance at 280 nm was collected and concentrated by pressure dialysis. The optical absorption spectrum of this material had maxima at 279 and 317 nm. The absorbance measurements indicated that about 4 moles of the NHPA were bound per mole of protein carrier, i.e., p=4.

Antibodies against the immunogen were obtained by mixing together about 1 mg of the NHPA bovine serum albumin immunogen prepared as described in B above in 0.5 ml of 0.1 M sodium phosphate buffer, pH 7.0, and 0.5 ml of Freunds adjuvant and injecting the mixture subcutaneously into a rabbit. Booster immunizations were administered at 4 week intervals. After optimal antibody titer was reached, the rabbit was bled to yield a suitable volume of antiserum specific to the administered immunogen.

C. Preparation of Labelled Conjugate (β-galactosylumbelliferone-NHPA)

A solution of 737 mg (2 mmol) of 7-β-galactosyl-coumarin-3-carboxylic acid and 202 mg (2 mmol) of triethylamine in 20 ml of dry DMF was cooled to −10° C. while stirring under an inert atmosphere. To this was added, all at once, 273 mg (2 mmol) of isobutyl chloroformate. After stirring for 20 minutes at −10° C., a white precipitate of triethylamine hydrochloride formed, indicating conversion of the acid to the mixed anhydride. It was combined with 631 mg (3 mmol) of the hydroxypropylamine prepared as described in A above, stirred 1 hour at −10° C., then allowed to warm to room temperature and stirred for an additional hour. The reaction mixture was diluted with 20 ml of DMF and 8 g of silica gel was added. The solvent was removed under high vacuum and the impregnated silica gel placed atop a column of 200 g of silica gel made up in ethyl acetate. The column was eluted with a gradient of 1 liter of ethyl acetate to 1 liter of ethanol and 10 ml fractions were collected. Fractions 109 to 135 were combined and evaporated. The residue was recrystallized from methanol to give 450 mg (39 percent yield) of the desired labelled conjugate designated as βGU-NHPA, as tan crystals, mp 200°–210° C. (gradual softening).

The efficacy of the 3-(1-naphthoxy)-2-hydroxypropylamine -bovine serum albumin immunogen prepared as described in B above in producing antibodies which are specific to propranolol was determined by the following procedure.

Titration of Antibodies to NHPA

Antibody binding reactions were carried out in 3.05 ml of 0.05 M N,N-bis-(2-hydroxyethyl)-glycine buffer, commercially available from Calbiochem-Behring, LaJolla, Calif., under the trade designation Bicine, ph 8.5, containing 0.016 percent (v/v) of a detergent, for example, polyoxyethylene sorbitan monooleate, commercially available from J. T. Baker, Phillipsburg, N.J., under the trade designation Tween 20, and the labelled conjugate prepared as described in C above at a level which gives an absorbance of 0.00023 at 340 nm. Various volumes of antiserum obtained as described in B were added to appropriate reaction mixtures and then 0.05 ml of β-galactosidase, 0.5 Unit per ml, was added to each reaction mixture. One unit of β-galactosidase hydrolyzes one micromole of β-D-galactosyl-orthonitrophenol per min. at 25° C. The reactions were allowed to stand at ambient temperature for 30 minutes and then the fluorescence was recorded using 400 nm light for excitation and 450 nm for emission. Controls with all reagents except β-galactosidase were carried through the procedure to provide the background fluorescence values which were substracted from the fluorescence measured for the reactions. The results are summarized in Table I below.

TABLE I

| Antiserum μl | Net Fluorescence |
|---|---|
| 0 | 80 |
| 2 | 46 |
| 5 | 20 |
| 10 | 8 |
| 20 | 3 |

The labelled conjugate, i.e., βGU-NHPA, is cleaved by the enzyme β-galactosidase to release a fluorescent product. When bound by antibody to the hydroxypropylamine, the conjugate is rendered inactive as a substrate for the enzyme.

Therefore, a decrease in the fluorescence level as the level of antiserum (antibodies) increases indicates that antibodies produced by the immunogen bind to the labelled conjugate.

The antibody-fluorescence relationship shown in Table I above was used to establish a substrate-labelled fluorescent immunoassay (SLFIA) for propranolol as described below.

SLFIA

The SLFIA is based on a competitive binding of antibodies to propranolol and the labelled conjugate, βGU-hydroxypropylamine, i.e., βGU-NHPA. The following reagents were prepared.

Antibody/Enzyme Reagent

Competitive binding reactions (3.1 ml) were set up in a series of cuvettes containing 50 mM glycine buffer, pH 8.5, 0.016 percent monooleate detergent, various levels of propranolol, and N-3-(1-naphthoxy)-2-hydroxypropyl-7-β-galactosyl-coumarin-3-carboxamide, at a level which gave an absorbance of 0.00023 at 340 nm. Ten microliters of antiserum were added to each cuvette and the contents were mixed. A 50 ml portion of β-galactosidase (0.5 unit/ml) was added and the reactions were incubated at ambient temperature for 30 minutes. Thirty minutes after addition of the enzyme to each cuvette, the fluorescence was recorded. Controls were also set up without the enzyme; the fluorescence measured for the controls was subtracted from the values for the corresponding enzyme reaction.

The following assay results shown below in Table II were obtained.

TABLE II

| Propranolol in assay (nM) | Net Fluorescence |
| --- | --- |
| 0 | 9 |
| 32 | 12 |
| 158 | 28 |
| 604 | 49 |

The competitive binding assay method utilizes the amount of binding between the propranolol and antibody (Ab) (to form Ab-propranolol conjugate) and the amount of binding between the βGU-NHPA and Ab (to form Ab-βGU-NHPA conjugate). If the amount of propranolol present can be used to determine the amount of relief of inhibition of fluorescence, the assay system is sufficiently sensitive to measure the amount of propranolol present in a sample. As shown in Table II, as the amount of propranolol was increased, the inhibition of fluorescence by the antiserum present was relieved, and the amount of fluorescence increased. Thus an assay was provided for determining the amount of propranolol present in a sample, using the reagents of the present invention.

EXAMPLE II

A. Preparation of 3-N-[2-Hydroxy-3-(1-naphthoxy)-1-propyl]aminobutyric Acid (NHAB)

A mixture of 2.61 g (11.0 mmol) the chlorohydrin prepared as described in Example I, A, 1.10 g (11 mmol) of 3-aminobutyric acid available from Aldrich Chemical Co., Milwaukee, Wis., U.S.A. and 1.85 g (22 mmol) of sodium bicarbonate in 50 ml of absolute ethanol was stirred at reflux temperature under an argon atmosphere for two days.

Silica gel 60, commercially available from E. Merck AG, Darmstadt, Germany, 20 g, was added to the reaction mixture and the solvent was evaporated under high vacuum. The impregnated silica gel was placed atop a column of 300 g of silica gel 60 prepared in 95 percent ethanol. The chromatography was developed with 95 percent ethanol and 20 ml fractions were collected. Fractions 280 and 425 were combined and evaporated to give a pale yellow oil. The oil was dissolved in a small amount of methanol and allowed to stand for one week at room temperature. The NHAB product crystallized from solution and was collected by filtration to give 525 mg (15.7 percent yield) of a white solid which melted at 196° C.

Analysis: Calculated for: $C_{17}H_{21}NO_4$: C, 67.31; H, 6.98; N, 4.62. Found: C, 66.88; H, 6.86; N, 4.61.

Infrared spectrum (KCl): 1600 cm$^{-1}$ (C=O); 1580 cm$^{-1}$ (C=O).

B. Preparation of 3-N-[2-Hydroxy-3-(naphthoxy)-1-propyl]aminobutyric Acid Bovine Serum Albumin Immunogen The NHAB prepared as described in A above was coupled to methylated bovine serum albumin by the following procedure (cf. C. Bohoun, et. al., *Clin. Chim. Acta*, 57, 263 (1974). To 2 ml of an aqueous solution of 90 mg of methylated bovine serum albumin (pH 5.5; 4° C.) [see J. D. Mandell and A. D. Hershey, *Anal. Biochem*, 1:66 (1960)] was added a slurry of 50 mg of 1-ethyl-3-(3-Dimethylaminopropyl) carbodiimide hydrochloride (Sigma Chemical Co., St. Louis, Mo. as a slurry in a solution of 15 mg of the carboxylic acid derivative in 0.2 ml of DMF. The final pH was adjusted to 5.5 and the reaction was stirred overnight in the dark at 4° C. The resulting NHAB immunogen conjugate can be purified by chromatography on Sephadex G-25 as previously described for the NHPA Immunogen conjugate.

Antibodies against the immunogen can be raised as previously described for the NHPA immunogen conjugate, Example I, B.

Optionally, as described below, antibodies against the immunogen of Example I can be used.

C. Preparation of Labelled Conjugate (β-galactosylumbelliferone-NHAB)

The labelled conjugate was prepared according to the following synthetic scheme, as described hereinafter.

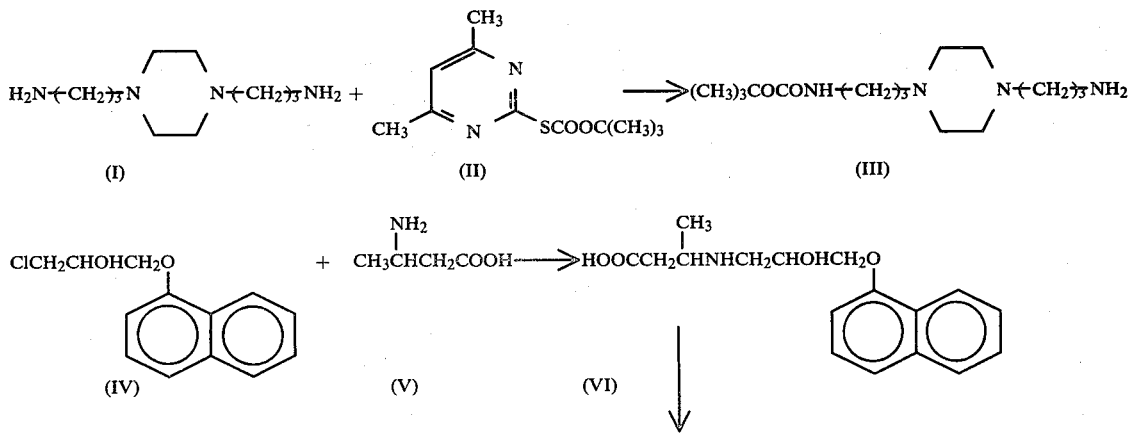

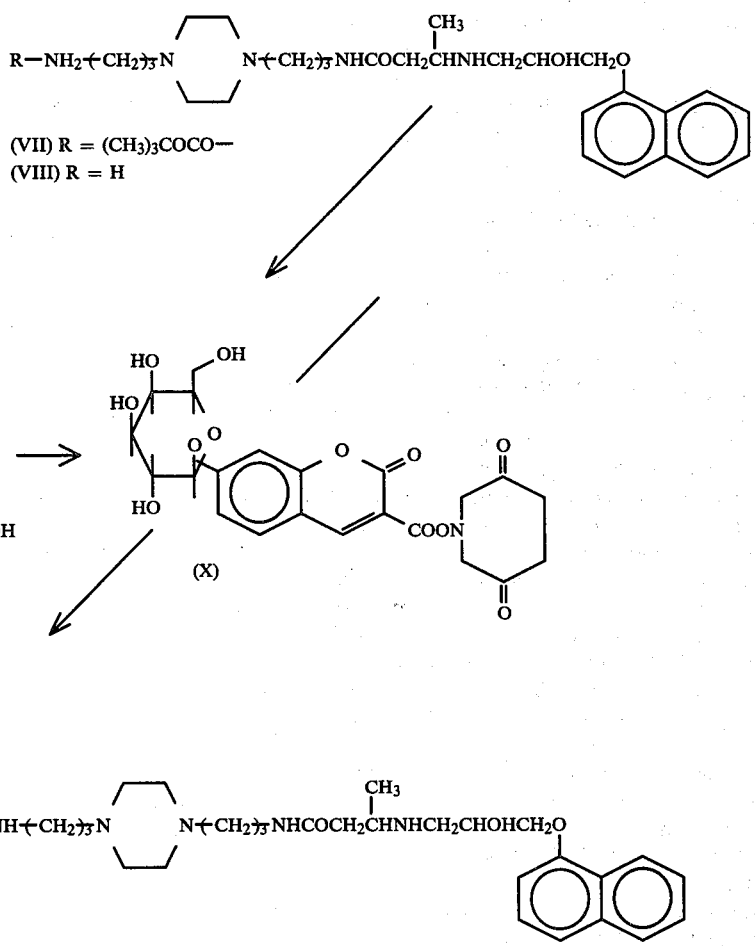

(VII) R = (CH₃)₃COCO—
(VIII) R = H

1-(3-Aminopropyl)-4-(-tert-butoxycarbonylaminopropyl)piperazine III

A solution of 100 g (0.42 mol) of tert-butyl S-(4,6-dimethylpyrimidin-2-yl) thiolcarbonate (II) available from Aldrich Chemical, in 400 ml of dry dioxane was added at room temperature, dropwise over a period of 6 hours, to a solution of 182 g (0.91 mol) of 1,4-bis-(3-aminopropyl) piperazine (I) in 360 ml of dioxane. After stirring overnight, the reaction was filtered and evaporated to give a yellow oil. It was dissolved in 2 liters of distilled water and applied to a 90 cm×5 cm column of Amberlite IRC-50 ion exchange resin (NH₄⊕ form). The column was washed with 500 ml of water, then eluted with a linear gradient of 2 liters of water to 2 liters of 0.5 M ammonium hydroxide. The appropriate fractions were pooled and evaporated to give 65 g of the amine (III) as a light-yellow oil.

Analysis: Mass Spectrum (70 e.V.): m/e 301 [MH⁺]; 201 [MH⁺ minus COOC(CH₃)₃].

1-[3-tert-Butoxycarbonylamino)propyl]-4-[[[3-[[3-[N-(1-naphthoxy-2-hydroxypropyl)amino]butyramido]]-propyl]]]piperazine VII A mixture of 909 mg (3 mmol) of 3-N-[3-(1-naphthoxy-2-hydroxypropyl] aminobutyric acid (VI) and 1.2 g (4 mmol) of 1-(3-aminopropyl)-4(3-tert-butoxycarbonylaminopropyl) piperazine (III) was suspended in 35 ml of dry DMF and cooled to −10° C. while stirring under an inert atmosphere. To this was added 908 mg (3.3 mmol) of 98 percent diphenylphosphoryl azide. After 15 minutes at −10° C., the reaction was combined with 15 g of silicic acid and the solvent removed on a rotary evaporator attached to a vacuum pump. The impregnated absorbent was placed atop a column of 100 g of silicic acid made up in 95 percent ethanol. The column was eluted with a linear gradient of 2 liters of 95 percent ethanol to 2 liters of 7:3 (v/v) ethanol:1 M aqueous triethylammonium bicarbonate, and 20 ml fractions were collected. Fractions 65 through 80 were pooled and evaporated to give 650 mg (37 percent yield) of the piperazine (VII) as a clear oil.

1-[3-(7-β-Galactosylcoumarin-3-carboxamido)propyl]-4-[[[3-[[3-[N-(1-naphthoxy-2-hydroxypropyl)amino]-butyramido]]propyl]]]piperazine XI The tert-butoxycarbonylamino derivative (VII) (645 mg, 1.1 mmol) was placed in a 50 ml pear-shaped flask and cooled to −10° C. under an inert atmosphere. Anhydrous trifluoroacetic acid (20 ml) was added and the mixture stirred at this temperature for 3 hours. At the end of this time the solution was evaporated at 0° C. on a rotary evaporator attached to a vacuum pump. This left the trifluoroacetic acid salt of the amine (VIII) as a light red oil which was not characterized. It was taken up in 25 ml of water and the pH of the solution adjusted to 8.0 with NaOH solution.

A second solution was prepared by dissolving 410 mg (1.1 mmol) of 7-β-galactosylcoumarin-3-carboxylic acid (IX) [J. F. Burd, et. al., *Clin. Chem.*, 23(8): 1402 (1977)] and 250 mg (2.2 mmol) of N-hydroxysuccinimide in 15 ml of dry DMF. The solution was cooled to −10° C. and 252 mg (1.2 mmol) of dicyclohexylcarbodiimide was added. The cooling bath was removed and the contents of the flask allowed to warm to room temperature and stir for a total of 3 hours.

The aqueous solution of amine (VIII) (pH 8.0) was cooled to 0° C. and the DMF solution, now containing the activated ester (X), was added dropwise to it over a 10 minute period. The pH was then adjusted to 7.0 with NaOH solution and stirring continued overnight at room temperature. Fifteen grams of silicic acid was added and solvent removed under reduced pressure. The impregnated adsorbent was placed atop a column of 100 g of silicic acid made up on 95 percent ethanol. The column was washed with 500 ml of this solvent, then eluted with a linear gradient of 2 liters of 95 percent ethanol to 2 liters of 4:1 (v/v) 95 percent ethanol:1 M aqueous triethylammonium bicarbonate. Fifteen ml fractions were collected.

Fractions 35 through 60 were pooled and evaporated to give 420 mg of conjugate XI as a pale tan glass. It was taken up in 5 ml of methanol and applied to a column of Sephadex LH-20 (90 cm×2.5 cm) equilibrated in methanol. Elution was with methanol (flow rate 1.3 ml/min) while 10 ml fractions were collected.

Fractions 30 through 39 were combined, evaporated, and dried under high vacuum to give 200 mg (19 percent yield) of conjugate (XI) as a pale tan glass.

Analysis: Calculated for the bis-carbonate salt: $C_{45}H_{61}N_5O_{18}$: C, 55.72; H, 6.34; N, 7.22. Found: C, 54.98; H, 6.13; N, 7.00.

Mass Spectrum (field desorption): m/e 836 [M+]; 674 [M+ minus $C_6H_{10}O_5$].

Optical Rotation: $\alpha_D = -32.62°$ (c 1.0, $CH_3OH$).

Antibody Titration With XI

Antiserum to the 3-(1-naphthoxy)-2-hydroxypropylamine bovine serum albumin conjugate were titrated with XI. A series of cuvettes with 3.0 ml of 50 mM glycine buffer, pH 8.5, and 0 to 15 μl antiserum were set up. One hundred microliters of XI (absorbance at 340 nm was 0.011) in the glycine buffer with 0.003 percent of the monooleate detergent added to each cuvette and the contents were mixed. The 100 μl of β-galactosidase (0.005 units/ml) was added and the reactions were incubated at ambient temperature for 20 minutes. At the end of the incubation period the fluorescence was recorded using 400 nm light for excitation and 450 nm for emission.

| Antiserum (μl) | Net Fluorescence |
|---|---|
| 0 | 89 |
| 3 | 67 |
| 6 | 48 |
| 9 | 37 |
| 12 | 34 |
| 15 | 33 |

These results shown that the fluorescence decreased as the antiserum level increased.

Competitive Binding Assay Using XI

The following reagents were prepared: fluorogenic reagent—XI (absorbance at 340 nm was 0.011) in 5 mM sodium formate-formic acid buffer, pH 4.5, containing 0.003 percent Tween 20. Antibody/Enzyme reagent—β-galactosidase (0.005 units/ml) and 10.8 μl antiserum/ml of 50 mM glycine buffer, pH 8.5. Propranolol calibrator—one microgram propranolol per ml in 50 mM glycine buffer, pH 8.5.

Assay Procedure

Zero to 100 μl aliquots of the propranolol calibrator were added to a series of cuvettes containing 3.0 ml of 50 mM glycine buffer, pH 8.5. One hundred microliters of the antibody/enzyme reagent was added to each cuvette and the contents were mixed. Then 100 μl of the fluorogenic reagent was added and the reactions were allowed to stand at ambient temperature for 20 minutes. At the end of this incubation period, the fluorescence was recorded.

| Propranolol ng/assay | Net Fluorescence |
|---|---|
| 0 | 35 |
| 5 | 40 |
| 10 | 45 |
| 20 | 52 |
| 40 | 63 |
| 80 | 70 |
| 100 | 70 |

As the propranolol level increased, the fluorescence increased, indicating that the drug and compound XI competed for antibody binding sites.

What is claimed is:

1. A propranolol immunogen having the formula:

$$\left[ \text{naphthyl-OCH}_2\text{CHCH}_2\text{NHC}(\text{OH})(\text{CH}_2)_n\overset{\text{NH}_2^+}{\underset{\|}{C}}---\right]_p (\text{NH})\text{Carrier}$$

wherein—(NH)Carrier is an immunogenic carrier material coupled through amino groups, n is an integer from 2 to 10, and p is on the average from about 1 to 50.

2. The immunogen of claim 1 wherein the Carrier is a protein or peptide.

3. The immunogen of claim 1 wherein p is on the average from about 1 to 25.

4. The immunogen of claim 1 wherein the Carrier is bovine serum albumin.

5. The immunogen of claim 4 wherein n is 4.

6. An antibody prepared against the immunogen of claim 1.

7. An antibody prepared against the immunogen of claim 2.

8. An antibody prepared against the immunogen of claim 5.

* * * * *